US011554100B2

(12) United States Patent
Nivorozhkin et al.

(10) Patent No.: US 11,554,100 B2
(45) Date of Patent: *Jan. 17, 2023

(54) SINGLE-LAYER ORAL DOSE OF NEURO-ATTENUATING KETAMINE (71) Applicant: Amorsa Therapeutics, Inc., Littleton, MA (US)

(72) Inventors: Alex Nivorozhkin, West Roxbury, MA (US); Nelson Landrau, Marlborough, MA (US)

(73) Assignee: Amorsa Therapeutics, Inc., Littleton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/868,444

(22) Filed: May 6, 2020

(65) Prior Publication Data

US 2020/0261370 A1 Aug. 20, 2020

Related U.S. Application Data (63) Continuation of application No. 15/885,231, filed on Jan. 31, 2018, now Pat. No. 10,653,629, which is a continuation of application No. 14/914,416, filed as application No. PCT/US2014/052786 on Aug. 26, 2014, now Pat. No. 9,913,803.

(60) Provisional application No. 62/015,513, filed on Jun. 22, 2014, provisional application No. 61/869,884, filed on Aug. 26, 2013.

(51) Int. Cl.
*A61K 9/20* (2006.01)
*A61K 31/135* (2006.01)
*A61K 31/13* (2006.01)

(52) U.S. Cl.
CPC .......... *A61K 9/2059* (2013.01); *A61K 9/2013* (2013.01); *A61K 9/2027* (2013.01); *A61K 9/2031* (2013.01); *A61K 9/2054* (2013.01); *A61K 31/135* (2013.01); *A61K 31/13* (2013.01)

(58) Field of Classification Search
CPC ..... A61K 31/13; A61K 31/135; A61K 9/2054
See application file for complete search history.

(56) References Cited

U.S. PATENT DOCUMENTS

| 5,204,116 | A | 4/1993 | Edgren et al. |
| 6,194,000 | B1 | 2/2001 | Smith et al. |
| 6,855,735 | B2 | 2/2005 | Friedman |
| 9,073,819 | B2 | 7/2015 | Amin et al. |
| 9,913,803 | B2 | 3/2018 | Nivorozhkin et al. |
| 10,653,629 | B2 * | 5/2020 | Nivorozhkin ........... A61P 25/24 |

FOREIGN PATENT DOCUMENTS

| EP | 1103256 A1 | 5/2001 |
| JP | 2004520410 A | 7/2004 |
| JP | 2004528338 A | 9/2004 |
| JP | 2016537782 A | 12/2016 |
| WO | 2008118785 A2 | 10/2008 |
| WO | 2009131794 A1 | 10/2009 |
| WO | 2013/003669 A2 | 1/2013 |
| WO | 2014020155 A1 | 2/2014 |
| WO | 2015/031410 A1 | 3/2015 |

OTHER PUBLICATIONS

E. Tanner-Smith, "Pharmacological content of tablets sold as "ecstasy": Results from an online testing service", Elsevier Scientific Publishers, IR, Drug and Alcohol Dependence, 2006, vol. 83, pp. 247-254.
W. Cheng, et al., "Chemical Profiling of 3, 4-Methylenedioxymethamphetamine (MDMA) Tablets Seized in Hong Kong", Journal Of Forensic Sciences, Nov. 2003, vol. 48, No. 6.
K. Sherlock et al., "Analysis of illicit ecstacy tablets: implications for clinical management in the accident and emergency department", Emergency Medicine Journal, vol. 16, No. 3, May 1999, pp. 194-197.
C. Chong et al., "Development of a Sublingual/Oral Formulation of Ketamine for Use in Neuropathic Pain", Clinical Drug Investigation, 2009, vol. 29, No. 5, pp. 317-324.
Supplemental European Search Report issued in counterpart European Application No. 14840272.0, dated Feb. 24, 2017 (5 pages).
Search Opinion issued in counterpart European Application No. 14840272.0, dated Feb. 24, 2017 (4 pages).
Pending Claims issued in counterpart European Application No. 14840272.0, dated Feb. 24, 2017 (3 pages).
International Search Report issued in International Application No. PCT/2014/052786, dated Nov. 26, 2014 (2 pages).
International Preliminary Report on Patentability issued in International Application No. PCT/US2014/052786, dated Nov. 26, 2014 (9 pages).
Notification of Reason for Refusal issued in corresponding Japanese Patent Application No. 2016-537782, dated May 8, 2018, 8 pages.
Chong, et al., Development of a Sublingual/Oral Formulation of Ketamine for Use in Neuropathic Pain: Preliminary Findings from a Three-Way Randomized Crossover Study, Clin Drug Invest (2009) 8 pages.
Cheng, et al., Chemical Profiling of 3,4-Methylenedioxymethamphetamine (MDMA) Tablets Seized in Hong Kong, J. Forensic Sci, Nov. 2009, vol. 48, 11 pages.
Tanner-Smith, Emily, Pharmacological content of tablets sold as "ecstasy": Results from an online testing service, Drug and Alcohol Dependence (2005) 8 pages.

(Continued)

*Primary Examiner* — Kevin E Weddington
(74) *Attorney, Agent, or Firm* — Michael Best & Friedrich LLP (57) ABSTRACT

The present invention is directed to oral neuro-attenuating ketamine (NAKET) tablet formulations, and methods of administration, which ensure the steady release of a therapeutically effective concentration of ketamine from an oral tablet without neurologically toxic spikes in ketamine concentration. In particular, the present invention provides single layer oral tablet formulation of NAKET. In a specific embodiment, the NAKET tablet formulation, and methods of administration provide steady administration of NAKET to a subject for 24 hours or greater, for example, up to 36 hours, after a single administration event.

17 Claims, 5 Drawing Sheets

(56) References Cited

OTHER PUBLICATIONS

Yanagihara, Yoshitsugu, Studies on Development and Clinical Application of Ketamine Preparations for Neuropathic Pain Relief, Japanese Society of Pharmaceutical Health Care and Sciences, vol. 32, No. 4 (2006), 275-288.
Yanagihara, et al., Preparation of Ketamine Tablets for Treatment of Patients with Neuropathic Pain, Yakugaku Zasshi, vol. 119 (1999), pp. 980-987.
English langage summary of Notification of Reason for Refusal issued in counterpart Japanese Patent Application No. 2016-537782 dated Nov. 29, 2018.
English langage summary of Japanese Office Action Nov. 29, 2018 issued in counterpart Japanese Application No. 2016-537782.
European Patent Office examination report dated Apr. 25, 2019 issued in counterpart European Application No. 14840272.0.
Applicant response dated Jan. 14, 2019 filed in counterpart European Applicant No. 14840272.0.

* cited by examiner

SINGLE-LAYER ORAL DOSE OF NEURO-ATTENUATING KETAMINE

RELATED APPLICATIONS

This application is a Continuation Application of U.S. application Ser. No. 15/885,231 filed on Jan. 31, 2018 which is a Continuation Application of U.S. application Ser. No. 14/914,416 filed on Feb. 25, 2016 which is a national stage application, filed under 35 U.S.C. § 371, of International Application No. PCT/US2014/052786, filed on Aug. 26, 2014, and claims priority to U.S. Provisional Patent Application No. 61/869,884, filed on Aug. 26, 2013, and U.S. Provisional Patent Application No. 62/015,513, filed on Jun. 22, 2014, all of which, including their contents, are incorporated herein by reference in their entireties.

BACKGROUND OF THE INVENTION

Ketamine is a non-selective NMDA receptor antagonist that has been approved by FDA for induction and maintenance of the general anesthesia. It has also been shown effective in treating other conditions, for example, to alleviate different kinds of pain (Correll, 2003), depression (Zarate, 2012), acute brain injury and stroke (Heftle, 2012), epilepsy (Synowiec, 2013), alcohol dependence, Alzheimer's disease, asthma and other disorders.

The oral efficacy of ketamine for treatment of pain has been confirmed by multiple investigators and recently reviewed (Blonk, 2010). In most cases, ketamine was used as an oral solution prepared from the commercially available injectable formulation (1 or 10% ketamine in water), often times mixed with fruit juice or syrup for taste masking. Solid dose forms of ketamine have also been reported in several examples. In particular, Yanagihara et al. (Yanagihara 1999, 2003) reported preparation of oral tablets of ketamine by dry and wet granulation with pharmacokinetics in humans similar to the orally administered syrup formulation. Furthermore, oral and sublingual formulations of ketamine as gelatin-based lozenges having a total weight of 1 g and ketamine load of 25 mg have also been prepared by Chong (Chong, 2009).

When administered orally, ketamine is a subject to the first-pass liver metabolism via N-demethylation and conversion to the active metabolite Norketamine. The elimination half-life of ketamine has been estimated at 2-3 hours, and 4 hours for norketamine. Consequently, the therapeutic window of orally administered ketamine is relatively short, and prompts an oral administration of multiple daily doses of the drug, e.g., 3-5 times a day, to achieve desirable therapeutic effect.

Moreover, solid dose forms of ketamine have been consistently limited by their inability to provide therapeutically effective doses, even in the short-term, without neurologically toxic spikes in ketamine concentration. In fact, exceeding an optimal efficacy plasma concentration of the drug (10-300 ng/ml) leads to more pronounced side effects, such as sedation, hallucination, dizziness, and/or nausea, which can not only have immediate repercussions, but also effect treatment compliance.

In order to achieve the optimal therapeutic index, the most successful route of administration for maintaining the stable levels of the drug in the system over longer periods of time appears to be by infusion (Correll, 2004). Such administration affords direct titration control of the manner of the administration, and enables eliminating the presence of neurological side effects, e.g., resulting from psychotomimetic toxic plasma concentration spikes of ketamine. However, the process of infusion presents significant challenges in patient management, as well as the cost of the procedure, being difficult to administer outside of the Intensive Care Units (ICU).

As such, there remains a need for efficient, more convenient, and controllable ketamine formulations that mimic the results of ketamine infusion and afford no neurologically toxic (e.g., psychotomimetic toxic) plasma concentrations, and which address the identified gap in ketamine treatment of conditions such as pain, depression, traumatic brain injury, stroke, epilepsy, alcohol dependence, or Alzheimer disease.

SUMMARY OF THE INVENTION

The present invention is directed to oral neuro-attenuating ketamine (NAKET) tablet formulations providing improved safety profiles as compared with existing compositions of oral ketamine; as well as methods of administration, which ensure the steady release of a therapeutically effective concentration of ketamine from an oral tablet without psychotomimetic toxic spikes in ketamine concentration. In particular, the present invention provides single layer oral tablet formulations of NAKET. In certain specific embodiments, the NAKET tablet formulation, and methods of administration, provide steady administration of NAKET to a subject for 24 hours or greater, for example, up to 36 hours, after a single administration event.

Accordingly, one aspect the present invention provides a single-layer orally administered tablet composition, e.g., matrix composition, comprising neuro-attenuating ketamine (NAKET).

In another aspect, the present invention provides a method of treating a subject with ketamine comprising the step of administering to a subject a single-layer orally administered tablet composition of any formulation described herein comprising neuro-attenuating ketamine (NAKET), such that the subject is treated.

In yet another aspect, the present invention provides a method of continuous oral delivery of ketamine. The method comprises the steps of formulating ketamine into a single-layer tablet that provides a steady release of a therapeutically effective concentration of ketamine from an oral tablet over a complete release period with no neurologically toxic spikes, e.g., no sedative or psychotomimetic toxic spikes, in plasma ketamine concentration, to produce a neuro-attenuating ketamine (NAKET) single-layer tablet composition; and orally administering the NAKET single-layer tablet composition to a subject, such that the NAKET provides a continuous therapeutically effective concentration of ketamine to the subject.

Another aspect of the invention provides a method of formulating ketamine to ensure the steady release of a therapeutically effective concentration of ketamine from an oral tablet without neurologically toxic spikes, e.g., sedative or psychotomimetic toxic spikes, in plasma ketamine concentration comprising the step of combining (i) a water-insoluble neutrally charged non-ionic matrix; (ii) a polymer carrying one or more negatively charged groups; and (iii) ketamine, to produce a neuro-attenuating ketamine single-layer orally administered tablet composition.

An additional aspect of the invention provides a kit for the treatment of a subject with ketamine comprising a single-layer orally administered tablet composition of any formulation described herein comprising neuro-attenuating ketamine (NAKET), and instructions for use in the treatment of pain, e.g., wherein the instructions for use form an integrated component of the packaging for the tablet composition.

An additional aspect of the invention provides a kit for the treatment of a subject with ketamine comprising a single-layer orally administered tablet composition of any formulation described herein comprising neuro-attenuating ketamine (NAKET), and instructions for use in the treatment of brain injury, e.g., wherein the instructions for use form an integrated component of the packaging for the tablet composition.

An additional aspect of the invention provides a kit for the treatment of a subject with ketamine comprising a single-layer orally administered tablet composition of any formulation described herein comprising neuro-attenuating ketamine (NAKET), and instructions for use in the treatment of depression, e.g., wherein the instructions for use form an integrated component of the packaging for the tablet composition.

DETAILED DESCRIPTION OF THE INVENTION

The market for ketamine for the treatment of conditions such as pain or depression, or use in migraine (e.g., with aura), refractory asthma, alcohol dependence, epilepsy, brain injury and/or stroke, has been largely focused on injections or infusion administration mainly due to the consequences of exceeding certain plasma concentrations, beyond which serious neurological side effects result. Tablet or capsule formulations of ketamine have generally failed commercially due to the relatively short therapeutic window of orally administered ketamine, which requires an oral administration of multiple daily doses of the drug; and the increased likelihood of exceeding psychotomimetic toxic plasma concentrations of ketamine. And although sustained release formulations have been generally considered for essentially all drugs, it is the implementation of this formulation that takes inventive contribution, and has yet to be achieved for ketamine. Such evidence could not be clearer than from the large commercial need that remains in the market.

In this regard, current professionals are eager for alternatives to ketamine intravenous infusion for 24-hour therapeutically effective plasma concentration profile, while seeking to utilize the long-studied and predictable nature of ketamine as a therapeutic. However, even intricate, stratified tablets of other NMDA receptor antagonists such as dextromethorphan or amantadine that offer delayed release of a core material subsequent to the release of a separately formulated outer layer have not been able to achieve the release of an NMDA receptor antagonist for periods greater than 12 hours.

As confirmation, several common matrixes of the inactive pharmaceutical ingredients known in the art for the efficient controlled release were tested, and were unable to achieve 24 hour release profile. Using a controlled release matrix comprised of the hydroxypropyl methylcellulose and starch, a complete release of ketamine was observed in about 12 hours. Further, in the lipid-based matrices containing as much as 20% of Compritol ATO 888 (Glycerol behenate, Gattesfosse), ketamine could not be retained for more than 4-6 hours.

However, in order to maintain a therapeutically effective drug concentration in a once-a-day application analogous to the ketamine infusion, but which is more convenient for the patient care, ketamine release should approach 24 hours, and in a manner that does not afford spikes in ketamine plasma concentration. As such, the present invention provides oral neuro-attenuating ketamine (NAKET) tablet formulations, methods of treatment, and methods of administration, which ensure the steady release of a therapeutically effective concentration of ketamine from an oral tablet without sedative or psychotomimetic toxic spikes in ketamine concentration. In particular, the present invention provides single layer oral tablet formulation of NAKET. In certain specific embodiment, the NAKET tablet formulation, and methods of administration provide steady administration of NAKET to a subject for 24 hours or greater, for example, up to 36 hours, after a single administration event, e.g., oral administration of a designated amount of the formulation, whether in one pill, or multiple pills. In certain embodiments, however, reduction of this therapeutic window may be desirable in order to achieve certain advantages for these NAKET tablet formulations, such as tamper resistance.

The present invention, including methods, and pharmaceutical compositions/formulations will be described with reference to the following definitions which, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The term "ketamine," as used alone herein, is art-recognized, and is the common name for the molecule: (R,S)-2-(2-chlorophenyl)-2-(methylamino) cyclohexanone, or Ketamine Ketamine is a well-known drug that is very water-soluble (e.g., solubility of the ketamine hydrochloride in water is about 200 mg/ml), and therefore has a high propensity to be rapidly released from a polymer matrix. The term "ketamine" is intended to include both racemic and enantiomerically enriched, e.g. enantiomerically pure, forms. In certain embodiments, the ketamine is racemic ketamine. In certain embodiments, the ketamine is enantiomerically enriched in one enantiomer. In particular embodiments, the ketamine is enriched in the S enantiomer. In particular embodiments, the ketamine is enriched in the R enantiomer.

The term "norketamine," as used alone herein, is art-recognized, and is the common name for the molecule: (R,S)-2-(2-chlorophenyl)-2-(amino) cyclohexanone, or Norketamine Norketamine is a metabolic product of the demethylation of ketamine, and is considered by many to have activity and clearance similar to that of ketamine. The term "norketamine" is intended to include both racemic and enantiomerically enriched, e.g. enantiomerically pure, forms. In certain embodiments, the norketamine is racemic ketamine. In certain embodiments, the norketamine is enantiomerically enriched in one enantiomer. In particular embodiments, the norketamine is enriched in the S enantiomer. In particular embodiments, the norketamine is enriched in the R enantiomer.

As used herein, the language "maximum sustained release" describes the release window for certain formulations of the present invention formulated to increase the release period to a maximum value, which is ultimately limited by the time the gastrointestinal tract naturally excretes all drugs with food.

The language "tamper resistance" is art-recognized to describe aspects of a drug formulation that make it more difficult to use the formulation to abuse the drug moiety of the formulation through extraction for intravenous use, or crushing for freebase use; and therefore reduce the risk for abuse of the drug.

As used herein, the term "steady" describes the stable or steady-state level of a molecule concentration, e.g., ketamine concentration.

As used herein, the term "composition" is equivalent to the term "formulation."

As used herein, the language "administration event" describes the administration of a subject a given dose, in the form of one or more pills within a short window of time, e.g., less than 10 minutes.

As used herein, the language "release period" describes the time window in which the neuro-attenuating ketamine is released from the matrix to afford plasma concentrations of ketamine and norketamine. The start time of the release period is defined from the point of oral administration to a subject, which is considered nearly equivalent to entry into the stomach, and initial dissolution by gastric enzymes and acid.

As used herein, and unless otherwise specified, the terms "treat," "treating" and "treatment" refer to the eradication or amelioration of a disease, disorder, or condition, or of one or more symptoms associated with the disease, disorder or condition. In certain embodiments, the terms refer to minimizing the advancement or worsening of the disease, disorder, or condition resulting from the administration of a formulation of the invention to a patient with such a disease, disorder, or condition. In some embodiments, the terms refer to the administration of a formulation provided herein, after the onset of symptoms of the particular disease, disorder, or condition. The terms "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treating", "treatment", or the like, covers the treatment of a disease, disorder, or condition in a mammal, e.g., a primate, e.g., a human, and includes at least one of (i), (ii), and (iii) above. As is known in the art, adjustments for age, body weight, general health, sex, diet, time of administration, drug interaction and the severity of the condition may be necessary, and will be ascertainable with routine experimentation by one of ordinary skill in the art based on the invention described herein.

As used herein, the terms "subject", and "patient" are used interchangeably. The terms "subject" and "patient" refer to an animal (e.g., a bird such as a chicken, quail or turkey) or a mammal including non-primates a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and "prevention" refer to the prevention of the onset, recurrence or spread of a disease, disorder, or condition, or of one or more symptoms thereof. In certain embodiments, the terms refer to the administration of neuro-attenuating ketamine (NAKET) to a subject, with or without other additional active compounds, prior to the onset of symptoms, particularly to patients at risk of a disease, disorder, or condition provided herein. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term. "prophylactic treatment." In certain embodiments, the prevention is achieved by administration of a prophylactically effective amount of neuro-attenuating ketamine (NAKET) of the invention.

As used herein, and unless otherwise specified, a "therapeutically effective amount" of an active agent, e.g., neuro-attenuating ketamine (NAKET), is an amount sufficient to provide a therapeutic benefit in the treatment or management of a disease, disorder, or condition, or to delay or minimize one or more symptoms associated with the disease, disorder, or condition. A therapeutically effective amount of neuro-attenuating ketamine (NAKET) means an amount of neuro-attenuating ketamine (NAKET), alone or in combination with other therapies, which provides a therapeutic benefit in the treatment or management of the disease, disorder, or condition. The term "therapeutically effective amount" can encompass an amount that improves overall therapy, reduces or avoids symptoms or causes of disease, disorder, or condition, or enhances the therapeutic efficacy of another therapeutic agent. The therapeutically effective amount for a particular patient in need of such treatment can be determined by considering various factors, such as the condition treated, the overall health of the patient, method of administration, the severity of side-effects, and the like.

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term "managing" encompasses treating a subject who had suffered from the particular disease, disorder, or condition in an attempt to prevent or minimize the recurrence of the disease, disorder, or condition.

As used herein, and unless otherwise specified, a "prophylactically effective amount" of an active agent, e.g., neuro-attenuating ketamine (NAKET), is an amount sufficient to prevent a disease, disorder, or condition, or prevent its recurrence. A prophylactically effective amount of neuro-attenuating ketamine (NAKET) means an amount of neuro-attenuating ketamine (NAKET), alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The language "neurologically toxic spikes" is used herein to describe spikes in concentration of ketamine and/or norketamine that would produce side-effects of sedation or psychotomimetic effects, e.g., hallucination, dizziness, and nausea; which can not only have immediate repercussions, but also effect treatment compliance. In particular, ketamine side effects may become more pronounced at blood concentration levels above 300 ng/L.

II. Formulations of the Invention

One embodiment of the present invention provides a single-layer orally administered tablet composition comprising neuro-attenuating ketamine (NAKET), e.g., with reduced neurological adverse effects compared to existing oral formulations. For clarity, the "neuro-attenuating ketamine (NAKET)" utilized in the present invention is ketamine formulated to ensure the steady release of a therapeutically effective concentration of ketamine from an oral tablet without sedative or psychotomimetic toxic spikes in ketamine concentration. Such spikes in ketamine concentration have been well-documented to have serious psychotomimetic directed side effects including, but not limited to hallucination, dizziness, and nausea; which can not only have immediate repercussions, but also effect treatment compliance. In this regard, the present invention provides novel and inventive formulations comprising optimal matrices discovered for the long-term steady release of ketamine, with reduced sedative and psychotomimetic side effects.

In certain embodiments, the neuro-attenuating ketamine is psychotomimetic-attenuating ketamine (PAKET), wherein the neurologically toxic spikes are psychotomimetic toxic spikes, including but are not limited to hallucination, dizziness, and nausea.

In certain embodiments of the present invention, the tablet composition is adapted for maximum sustained release.

In certain embodiments of the present invention, the tablet composition is adapted for tamper resistance. In particular embodiments, the tablet composition comprises polyethylene oxide (PEO), e.g., MW 2,000 to 7,000 KDa, in combination with HPMC. In particular embodiments, the tablet composition may further comprise polyethylene glycol (PEG), e.g., PEG 8K. In particular embodiments, the tablet composition may further comprise polymer carrying one or more negatively charged groups, e.g., polyacrylic acid. In specific embodiments, the tablet composition comprising PEO is further subjected to heating/annealing, e.g., extrusion conditions.

In certain embodiments of the present invention, the NAKET comprises a combination of (i) a water-insoluble neutrally charged non-ionic matrix; (ii) a polymer carrying one or more negatively charged groups; and (iii) ketamine.

In certain embodiments of the present invention, the polymer carrying one or more negatively charged groups is selected from the group consisting of polyacrylic acid, polylactic acid, polyglycolic acid, polymethacrylate carboxylates, cation-exchange resins, clays, zeolites, hyaluronic acid, anionic gums, salts thereof, and mixtures thereof. In particular embodiments, the anionic gum is selected from the group consisting of naturally occurring materials and semi-synthetic materials. In a specific embodiment, the naturally occurring material is selected from the group consisting of alginic acid, pectin, xanthan gum, carrageenan, locust bean gum, gum arabic, gum karaya, guar gum, and gum tragacanth. In another specific embodiment, the semi-synthetic material is selected from the group consisting of carboxymethyl-chitin and cellulose gum.

Moreover, without wishing to be bound by theory, in certain embodiments, the role of the polymer carrying one or more negatively charged groups, e.g., moieties of acidic nature as in those of the acidic polymers described herein, surprisingly offers significant retention of ketamine in the matrix. In particular embodiments, this negative charge may be created in situ, for example, based on release of a proton due to pKa and under certain pH conditions or through electrostatic interaction/creation of negative charge. Further noting that acidic polymers may be the salts of the corresponding weak acids that will be the related protonated acids in the stomach; which, and without wishing to be bound by theory, will neutralize the charge and may reduce ketamine interactions with the matrix. In addition, the release matrix may be further complemented by other inactive pharmaceutical ingredients to aid in preparation of the appropriate solid dose form such as fillers, disintegrants, flow improving agents, lubricants, colorants, taste maskers.

In certain embodiments of the present invention, the tablet composition is adapted for tamper resistance. In particular embodiments, the tablet composition comprises polyethylene oxide (PEO), e.g., MW 2,000 to 7,000 KDa. In specific embodiments, the tablet composition comprising PEO is further subjected heating/annealing, e.g., extrusion.

In certain embodiments of the present invention, the non-ionic matrix is selected from cellulose-based polymers such as HPMC, alone or enhanced by mixing with components selected from the group consisting of starches; waxes; neutral gums; polymethacrylates; PVA; PVA/PVP blends; and mixtures thereof.

In certain embodiments of the present invention, the cellulose-based polymer is hydroxypropyl methylcellulose (HPMC). In a specific embodiment, the tablet composition comprises 20-60% hydroxypropyl methylcellulose, starch 10-30%, or any combination thereof.

In certain embodiments of the present invention, the tablet composition comprises an amount of ketamine therapeutically effective for the treatment of pain. In particular embodiments of the invention, the pain treated is cancer pain, e.g., refractory cancer pain. In particular embodiments of the invention, the pain treated is post-surgical pain. In particular embodiments of the invention, the pain treated is orthopedic pain. In particular embodiments of the invention, the pain treated is back pain. In particular embodiments of the invention, the pain treated is neuropathic pain. In particular embodiments of the invention, the pain treated is dental pain. In particular embodiments of the invention, the pain treated is chronic pain in opioid-tolerant patients.

In certain embodiments of the present invention, the tablet composition comprises an amount of ketamine therapeutically effective for the treatment of depression.

In certain embodiments of the present invention, the tablet composition comprises an amount of ketamine therapeutically effective for the treatment of brain injury.

In certain embodiments of the present invention, the tablet composition comprises an amount of ketamine therapeutically effective for the treatment of stroke.

In certain embodiments of the present invention, the tablet composition comprises an amount of ketamine therapeutically effective for use in migraine, e.g., with aura.

In certain embodiments of the present invention, the tablet composition comprises an amount of ketamine therapeutically effective for use in refractory asthma.

In certain embodiments of the present invention, the tablet composition comprises an amount of ketamine therapeutically effective for use in treating alcohol dependence.

In certain embodiments of the present invention, the tablet composition comprises an amount of ketamine released from the matrix with a rate 0.05-2 mg/kg/h over a period of 12-24 hours, e.g., 24 hours.

In certain embodiments of the present invention, the neuro-attenuating ketamine achieves a combined concentration of ketamine and its metabolite norketamine in plasma in the range of 10-500 ng/ml, and maintains this concentration for duration of the release period. In particular embodiments, the neuro-attenuating ketamine achieves a combined concentration of ketamine and its metabolite norketamine in plasma in the range of 10-300 ng/ml, and maintains this concentration for duration of the release period. In particular embodiments, the neuro-attenuating ketamine achieves a combined concentration of ketamine and its metabolite norketamine in plasma in the range of 10-100 ng/ml, and maintains this concentration for duration of the release period. In particular embodiments, the neuro-attenuating ketamine achieves a combined concentration of ketamine and its metabolite norketamine in plasma in the range of 10-20 ng/ml, and maintains this concentration for duration of the release period.

In certain embodiments of the present invention, the release period of the NAKET in the formulations of the invention is greater than 4 hours.

In certain embodiments of the present invention, the release period of the NAKET in the formulations of the invention is greater than 8 hours.

In certain embodiments of the present invention, the release period of the NAKET in the formulations of the invention is greater than 12 hours.

In certain embodiments of the present invention, the release period of the NAKET in the formulations of the invention is greater than 16 hours.

In certain embodiments of the present invention, the release period of the NAKET in the formulations of the invention is greater than 20 hours.

In certain embodiments of the present invention, the release period of the NAKET in the formulations of the invention is greater than (or equal to) 24 hours.

In certain embodiments of the present invention, the release period of the NAKET in the formulations of the invention is greater than (or equal to) 28 hours.

In certain embodiments of the present invention, the release period of the NAKET in the formulations of the invention is greater than (or equal to) 32 hours.

In certain embodiments of the present invention, the release period of the NAKET in the formulations of the invention is greater than (or equal to) 36 hours.

In certain embodiments of the present invention, the release period of the NAKET in the formulations of the invention is less than 48 hours.

In certain embodiments of the present invention, the release period of the NAKET in the formulations of the invention is less than 36 hours.

In certain embodiments of the present invention, the tablet compositions of the present invention are utilized as a 2-times a day application.

In certain embodiments of the present invention, the tablet compositions of the present invention are utilized as a once a day application.

In certain embodiments of the present invention, the tablet compositions are enhanced. In particular embodiments, due to the efficiency of administration, the formulation is able to utilize less ketamine for treatment to achieve the same effect as comparative tablets not described by the present invention.

In certain embodiments of the present invention, the oral administration event, which provides the appropriate single unit dose, may comprise one single pill or multiple pills.

In addition, to protect the tablet from the acidic environment in the stomach and maintain a long-term release, various types of enteric coating may be used in certain embodiments.

In certain embodiments of the present invention, single-layer tablet is coated with protective layers of inactive pharmaceutical ingredients, e.g., to ensure steady release of the drug from the matrix and avoid concentration bursts at the early release time points.

Another embodiment of the present invention provides formulation of ketamine that ensures the steady release of a therapeutically effective concentration of ketamine from an oral tablet without sedative or psychotomimetic toxic spikes in plasma ketamine concentration comprising ketamine formulated in an osmotic controlled release tablet. In these formulations a single core layer containing ketamine (e.g., as defined by other tablet formulations described herein) is surrounded by semi-permeable membrane with or without drug delivery orifice. Without wishing to be bound by theory, because these systems use water osmotic pressure for the controlled delivery of the active material, delivery rates are expected to be independent of gastrointestinal conditions. In combination with the novel and inventive aspects of the present invention, osmotic asymmetric-membrane technology or AMT (i.e., technology directed to a single-layer tablet coated with an insoluble, asymmetric microporous membrane produced by controlled phase separation) may be used to produce formulations useful in the methods of treatment and kits described herein.

Given the currently understood equivalent nature of norketamine to ketamine in terms of activity and clearance profiles, in certain embodiments, the present invention includes any composition described herein to comprise ketamine with reduced sedative and psychotomimetic side effects, wherein the ketamine is replaced by norketamine in equivalent amounts and forms, to produce tablet compositions comprising norketamine with reduced sedative and psychotomimetic side effects; and is equivalently useful in the methods and kits of the present invention. Such embodiments would include small variations that would be ascertainable by the ordinarily skilled artisan, in light of the descriptions provided herein.

In addition, in certain embodiments, the ketamine or norketamine may be derivatized in any manner that does not significantly effect formulation as described herein for ketamine, or the ability of the ketamine/norketamine to achieve the desired therapeutic effects described herein, i.e., with similar steady release of a therapeutically effective concentration (e.g., based on indication) of the ketamine derivative from an oral tablet without sedative or psychotomimetic toxic spikes in ketamine or ketamine derivative concentration. For example, the ketamine or norketamine may be deuterated, e.g., as described in U.S. Pat. No. 7,638,651, which is incorporated herein by reference hereto (and which indicates that such derivatives are expected to behave similarly to ketamine, and achieve results similar to ketamine).

In certain embodiments of the invention, the ketamine or norketamine may be formulated as a pharmaceutically acceptable salt thereof, e.g., ketamine hydrochloride, ketamine aspartate, ketamine succinate, etc, such that the ketamine/norketamine counterion does not significantly effect formulation as described herein for ketamine/norketamine, or the ability of the ketamine/norketamine to achieve the desired therapeutic effects described herein, i.e., with similar steady release of a therapeutically effective concentration (e.g., based on indication) of the ketamine derivative from an oral tablet without sedative or psychotomimetic toxic spikes in ketamine or ketamine derivative concentration. Exemplary salts, within this scope, may include but are not limited to: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art. Additional examples may include salts with inorganic cations such as sodium, potassium, calcium, magnesium, lithium, aluminum, zinc, etc; and salts formed with pharmaceutically acceptable amines such as ammonia, alkylamines, hydroxyalkylamines, lysine, arginine, N-methylglucamine, procaine and the like. In specific embodiments, the pharmaceutically acceptable salt is a hydrochloride salt.

Another embodiment of the present invention provides a kit for the treatment of a subject with ketamine comprising a single-layer orally administered tablet composition of any one of formulations described herein comprising neuro-attenuating ketamine (NAKET), and instructions for use in the treatment of pain, e.g., as described herein.

In particular embodiments of the invention, the pain treated is cancer pain, e.g., refractory cancer pain.

In particular embodiments of the invention, the pain treated is post-surgical pain.

In particular embodiments of the invention, the pain treated is orthopedic pain.

In particular embodiments of the invention, the pain treated is back pain.

In particular embodiments of the invention, the pain treated is neuropathic pain.

In particular embodiments of the invention, the pain treated is dental pain.

In particular embodiments of the invention, the pain treated is chronic pain in opioid-tolerant patients.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of brain injury.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of depression.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of migraine, e.g., with aura.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of refractory asthma.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of stroke.

Another embodiment of the present invention provides a kit for the treatment of a subject with ketamine comprising a single-layer orally administered tablet composition of any one of formulations of the present invention comprising neuro-attenuating ketamine (NAKET), and instructions for use in the treatment of alcohol dependence.

In certain embodiments of the kit, the instructions for use form an integrated component of the packaging for the tablet composition.

A. General Tablet Formulations of the Invention

The formulations of the invention comprise orally administered tablet compositions, which may include uncoated tablets or coated tablets (including film-coated, sugar-coated tablets, and gastro-resistant/enteric-coated tablets). Tablets for oral use may include the active ingredients, e.g., ketamine, mixed with pharmaceutically acceptable inactive excipients such as diluents, disintegrating agents, binding agents, lubricating agents, powder flow improving agent, wetting agents, sweetening agents, flavoring agents, coloring agents and preservatives. Moreover, tablets of the present invention are solid dosage forms intended for oral administration, obtained by dry granulation with single or multiple compressions of powders or granules. In certain embodiments, the tablets may be obtained by using wet granulation techniques. In certain embodiments, the tablets may be obtained by molding, heating/annealing, or extrusion techniques.

In certain embodiments, the tablets are right circular solid cylinders, the end surfaces of which are flat or convex, and the edges of which may be beveled. In particular embodiments, the surfaces are convex. In addition, they may have lines or break-marks (scoring), symbols or other markings.

In certain embodiments, the break-mark(s) is/are intended to permit accurate subdivision of the tablet in order to provide doses of less than one tablet. In certain embodiments of the invention, the tablet compositions comprise one or more excipients such as diluents, binders, disintegrating agents, glidants, lubricants, substances capable of modifying the behavior of the dosage forms and the active ingredient(s) in the gastrointestinal tract, coloring matter authorized by the appropriate, national or regional authority and flavoring substances. When such excipients are used it is necessary to ensure that they do not adversely affect the stability, dissolution rate, bioavailability, safety or efficacy of the active ingredient(s); there must be no incompatibility between any of the components of the dosage form.

Coated tablets are tablets covered with one or more layers of mixtures of substances such as natural or synthetic resins, polymers, gums, fillers, sugars, plasticizers, polyols, waxes, coloring matters authorized by the appropriate national or regional authority, and flavoring substances. Such coating materials do not contain any active ingredient, e.g., ketamine or norketamine. The tablets may be coated for a variety of reasons such as protection of the active ingredients from burst release from the matrix, air, moisture or light, masking of unpleasant tastes and odors or improvement of appearance. The substance used for coating may be applied as a solution or suspension.

In certain embodiments, the manufacturing processes for tablets meet the requirements of good manufacturing practices (GMP). In certain embodiments, one or more measures are taken in the manufacture of tablets selected from the following: ensure that mixing with excipients is carried out in a manner that ensures homogeneity; ensure that the tablets possess a suitable mechanical strength to avoid crumbling or breaking on subsequent processing, e.g., coating, storage and distribution; minimize the degradation of the active ingredient; minimize the risk of microbial contamination; minimize the risk of cross-contamination. In addition, in the manufacture of scored tablets (tablets bearing a break-mark or marks) for which subdivision is intended in order to provide doses of less than one tablet measures are taken to: ensure the effectiveness of break-marks with respect to the uniformity of mass or content, as appropriate, of the subdivided parts so that the patient receives the intended dose.

In general a suitable dose will be in the range of 0.01 to 10 mg per kilogram body weight of the recipient per day, preferably in the range of 0.1 to 5 mg per kilogram body weight per day. Additional details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition). For administration of the NAKET formulations, such labeling would include, e.g., instructions concerning the amount, frequency and method of administration.

B. Compliance with Monographs

In certain embodiments, the formulations of the present invention conform to certain industry accepted monographs to afford compliance with the Federal Food Drug and Cosmetic Act. In particular, the formulations of the present invention conform and are considered acceptable under visual inspection, uniformity of mass analysis, uniformity of content analysis, and/or dissolution/disintegration analysis all of which are established by a relevant monograph.

In certain embodiments, throughout manufacturing certain procedures are validated and monitored by carrying out appropriate in-process controls. These are designed to guarantee the effectiveness of each stage of production. In-process controls during tablet production may include the moisture content of the final lubricated blend, the size of granules, the flow of the final mixture and, where relevant, the uniformity of mass of tablet cores before coating. In-process controls during tablet production may also include the dimensions (thickness, diameter), uniformity of mass, hardness and/or crushing force, friability, disintegration or dissolution rate (for example, for modified-release tablets) of the finished dosage form. Suitable test methods that may be used to demonstrate certain of these attributes are known in the art.

In certain embodiments, packaging is required to be adequate to protect the tablets from light, moisture and damage during transportation.

In additional embodiments, the commercially available formulation (e.g., kit) complies with the labeling requirements established under Good Manufacturing Practices (GMP). Such label includes:
(1) the name of the pharmaceutical product;
(2) the name(s) of the active ingredient(s); International Nonproprietary Names (INN) should be used wherever possible;
(3) the amount of the active ingredient(s) in each tablet and the number of tablets in the container;
(4) the batch (lot) number assigned by the manufacturer;
(5) the expiry date and, when required, the date of manufacture;
(6) any special storage conditions or handling precautions that may be necessary;
(7) directions for use, warnings, and precautions that may be necessary;
(8) the name and address of the manufacturer or the person responsible for placing the product on the market;
(9) for scored tablets where the directions for use include subdivision to provide doses of less than one tablet, the label should also include:—the storage conditions for and the period of use of those subdivided part(s) not immediately taken or administered.

In certain embodiments, tablets are able to withstand handling, including packaging and transportation, without losing their integrity.

III. Methods of the Invention

The formulations of the invention may be used in the methods of the invention, e.g., methods of treatment of the invention. As such, the invention relates to the method of use of formulations of the invention, which contain neuro-attenuating ketamine (NAKET), e.g., for the treatment of pain. As such, in certain embodiments, the invention provides for the management of different kinds of pain, including but not limited to refractory cancer pain, neurologic pain, postoperative pain, complex regional pain syndrome (CRPS), migraine, e.g., with aura, and other conditions including depression, alcohol dependence, refractory asthma, epilepsy, acute brain injury and stroke, Alzheimer's disease and other disorders comprising an oral administration of the formulations of the present invention, described herein. In certain embodiments, the use of formulations of the present invention may be used as a standalone therapy. In certain embodiments, the use of formulations of the present invention may be used as an adjuvant/combination therapy.

In certain embodiments, the invention provides for the management of different kinds of pain, including but not limited to cancer pain, e.g., refractory cancer pain; neuropathic pain; opioid-induced hyperalgesia and opioid-related tolerance; neurologic pain; postoperative/post-surgical pain; complex regional pain syndrome (CRPS); shock; limb amputation; severe chemical or thermal burn injury; sprains, ligament tears, fractures, wounds and other tissue injuries; dental surgery, procedures and maladies; labor and delivery; during physical therapy; radiation poisoning; acquired immunodeficiency syndrome (AIDS); epidural (or peridural) fibrosis; orthopedic pain; back pain; failed back surgery and failed laminectomy; sciatica; painful sickle cell crisis; arthritis; autoimmune disease; intractable bladder pain; pain associated with certain viruses, e.g., shingles pain or herpes pain; acute nausea, e.g., pain that may be causing the nausea or the abdominal pain that frequently accompanies sever nausea; migraine, e.g., with aura; and other conditions including depression (e.g., acute depression or chronic depression), depression along with pain, alcohol dependence, acute agitation, refractory asthma, acute asthma (e.g., unrelated pain conditions can induce asthma), epilepsy, acute brain injury and stroke, Alzheimer's disease and other disorders. In addition, the present invention includes the treatment/management of any combination of these types of pain or conditions.

In certain embodiments, the pain treated/managed is acute breakthrough pain or pain related to wind-up that can occur in a chronic pain condition.

In particular embodiments of the invention, the pain treated/managed is cancer pain, e.g., refractory cancer pain.

In particular embodiments of the invention, the pain treated/managed is post-surgical pain.

In particular embodiments of the invention, the pain treated/managed is orthopedic pain.

In particular embodiments of the invention, the pain treated/managed is back pain.

In particular embodiments of the invention, the pain treated/managed is neuropathic pain.

In particular embodiments of the invention, the pain treated/managed is dental pain.

In particular embodiments of the invention, the condition treated/managed is depression.

In particular embodiments of the invention, the pain treated/managed is chronic pain in opioid-tolerant patients.

For example, in one embodiment, the invention provides a method of treating a subject with ketamine comprising the step of administering to a subject a single-layer orally administered tablet composition, e.g., matrix composition, of the present invention comprising neuro-attenuating ketamine (NAKET), such that the subject is treated.

The administering physician can provide a method of treatment that is prophylactic or therapeutic by adjusting the amount and timing of NAKET administration on the basis of observations of one or more symptoms of the disorder or condition being treated.

In another embodiment, the invention provides a method of continuous oral administration of ketamine comprising the steps of formulating ketamine into a single-layer tablet that provides a steady release of a therapeutically effective concentration of ketamine from an oral tablet over a complete release period with neurologically toxic spikes, e.g., no sedative or psychotomimetic toxic spikes in plasma ketamine concentration, to produce a neuro-attenuating ketamine (NAKET) single-layer tablet composition; and orally administering the NAKET single-layer tablet composition to a subject, such that the NAKET provides a continuous therapeutically effective concentration of ketamine to the subject.

In certain embodiments of the invention, the subject is a mammal.

In certain embodiments of the invention, the mammal is a human.

In another embodiment, the present invention provides a method of formulating ketamine to ensure the steady release of a therapeutically effective concentration of ketamine from an oral tablet without neurologically toxic spikes, e.g., sedative or psychotomimetic toxic spikes, in plasma ketamine concentration. In a particular embodiment, the method comprises the step of combining (i) a water-insoluble neutrally charged non-ionic matrix; (ii) a polymer carrying one or more negatively charged groups; and (iii) ketamine, to produce a neuro-attenuating ketamine single-layer orally administered tablet composition. In another particular embodiment, the method comprises the step of combining (i) polyethylene oxide (PEO), e.g., MW 2,000 to 7,000 KDa, with HPMC, and (ii) ketamine, to produce a neuro-attenuating ketamine single-layer orally administered tablet composition. In specific embodiments, wherein the method comprises the step of combining polyethylene oxide (PEO) with HPMC, and ketamine, the tablet composition may further comprise polyethylene glycol (PEG), e.g., PEG 8K., a polymer carrying one or more negatively charged groups, e.g., polyacrylic acid and/or may be further subjected to heating/annealing, e.g., extrusion conditions.

In certain embodiments, the formulations of the invention may be administered in combination with other active therapeutic agents, e.g., opioids to reduce pain. In particular embodiments, the formulations of the present invention serve to reduce the amount of opioids necessary to treat a patient.

In certain embodiments, the formulations of the invention are not administered in combination with other active therapeutic agents.

In certain embodiments, the formulations of the invention may be administered in combination with another formulation of ketamine, e.g., a fast release formulation of ketamine.

In another embodiment, the present invention provides a method of formulating ketamine to ensure the steady release of a therapeutically effective concentration of ketamine from an oral tablet without sedative or psychotomimetic toxic spikes in plasma ketamine concentration comprising formulation of ketamine in an osmotic controlled release tablet. In these formulations the single core layer containing ketamine is surrounded by semi-permeable membrane with or without drug delivery orifice. In certain embodiments, combination with the novel and inventive NAKET tablet formulations of the present invention and osmotic asymmetric-membrane technology or AMT (i.e., technology directed to a single-layer tablet coated with an insoluble, asymmetric microporous membrane produced by controlled phase separation) may be used to produce formulations useful in the methods and kits described herein.

EXEMPLIFICATION

The present invention is illustrated by the following examples, which are not intended to be limiting in any way.

Example 1

Formulation of the Controlled Release Ketamine Tablet Using a Matrix Based on HPMC and Starch Ketamine was formulated into a controlled release tablet form, composition KTM-1, by dry granulation using a controlled release matrix based on a combination of hydroxypropyl methyl cellulose (HPMC) Methocel KM100 CR and pre-gelatinized starch Starch 1500. Methocel, Starch 1500, ketamine and Cab-o-Sil (colloidal silicon dioxide) were coarsely mixed and passed through a 40-mesh screen to break-up agglomerates, Microcrystalline cellulose was then added and the mixture blended in a 100 ml tube blender for 15 minutes at 200 rev/min. The full composition of ketamine tablet KTM-1 is presented in Table 1.

After blending, magnesium stearate was added and blended for additional 3 minutes. The 200 mg convex-shaped tablets containing 20 mg of ketamine were compressed using a TDP tablet press and 9 mm dye. By applying a compression force of 8 kN, the tablets of the hardness in the range 13-15 kP were generated. The tablet dissolution was carried out in a Type II dissolution apparatus (paddle) (Distek Premiere 5100 Dissolution System, Distek Inc., North Brunswick, USA) at 100 rpm, 37° C., using 1×PBS buffer, as an immersion media. Three tablets per batch were tested.

At predetermined time intervals, 1 ml samples were withdrawn (not replaced), filtered and assayed. The amount of ketamine released was measured by HPLC using an Agilent 1100 setup and UV detection at 210 nm. A 20 microliter sample volume was injected onto a Zorbax SB-Phenyl column, 4.6×150 mm, 5 microns, using as the mobile phase a mixture of 70% ammonium acetate (10 mM) and 30% acetonitrile; flow rate 1.5 ml/min; column temperature 40° C. Solutions of known concentrations of ketamine were used to calculate the amount of drug released.

Figure 1:
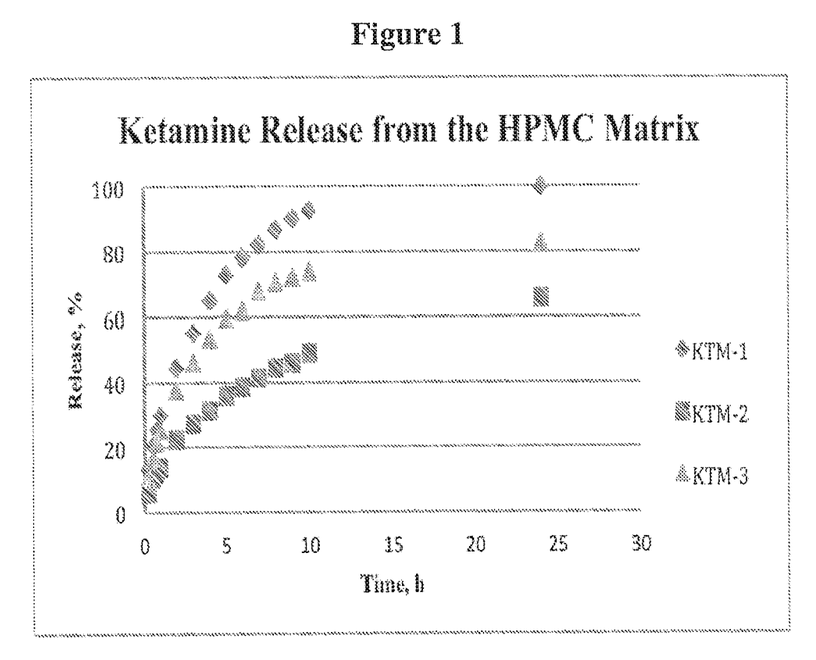
FIG. 1 is a graphical depiction of the release profile of ketamine from an HPMC matrix, with and without polyacrylic acid (compositions KTM-1 through KTM-3).

The method was linear in the range of concentration 0.001 to 0.5 mg/ml. Drug release was independent of the pH of the immersion media. A release at pH 1 and 6.8 displayed similar profiles. At 10 h time point, 92.5% of ketamine has been released (FIG. 1).

TABLE 1

Ketamine Tablet Compositions Based on the HPMC Matrix.

| Ingredient | Manufacturer's Brand | KTM-1 | KTM-2 | KTM-3 |
|---|---|---|---|---|
| HPMC | Methocel KM100 CR | 50.0% | 41.7% | 45.5% |
| Pre-gelatinized Starch | Starch 1500 | 19.0% | 15.8% | 17.3% |
| Microcrystalline Cellulose | Avicel PH-200 | 20.0% | 16.7% | 18.2% |
| Silica | Cabosil M-5P | 0.5% | 0.4% | 0.5% |
| Ketamine | Ketamine Hydrochloride | 10.0% | 8.3% | 9.1% |
| Polyacrylic Acid | Carbopol 974 NF | 0.0% | 16.7% | 9.1% |
| Mg Stearate | Spectrum | 0.5% | 0.4% | 0.5% |
| Total | | 100% | 100% | 100% |

Example 2

Formulation of the Neuro-Attenuating Ketamine Tablet Using HPMC and Polyacrylate Ketamine was formulated into a tablet form by dry granulation following the general procedure as described in the Example 1. The control formulation KTM-1 presented in Table 1 was supplemented by adding polyacrylic acid, Carbopol 974 NF (Noveon), for a total content of 16.7% and 9.1% to make compositions KTM-2 and KTM-3, respectively (See Table 1).

Consequently, this addition led to a surprisingly dramatic slowing down of the release (FIG. 1). Compared to the KTM-1, at the 10 hour time point KTM-2 showed only 49% of the drug was released; and at 24 hours 62% of the ketamine was released.

Moreover, reducing the level of Carbopol (i.e., polyacrylic acid) to about 9% in KTM-3 generated a release profile that matched closely to a window of 24-h, for once-a-day ketamine applications. The amount of the drug released at 24 h was 82%.

Composition KTM-3 was considered for development given typical acceleration of the release rate in vivo.

Example 3

Formulation of Sample 36 Hour Neuro-Attenuating Ketamine Tablet with Kollidon SR Based on the potential for additional in situ electrostatic interactions of ketamine with the polymer matrix to retain the drag, a polyvinylacetate/Povidone based polymer (Kollidon® SR) was elected. It consists of 80% Polyvinylacetate and 19% Povidone in a physical mixture, stabilized with 0.8% sodium lauryl sulfate and 0.2% colloidal silica. Kollidon SR possesses good compressibility and typically displays drug release profile independent of the dissolution medium (pH and salt/ion content).

Figure 2:
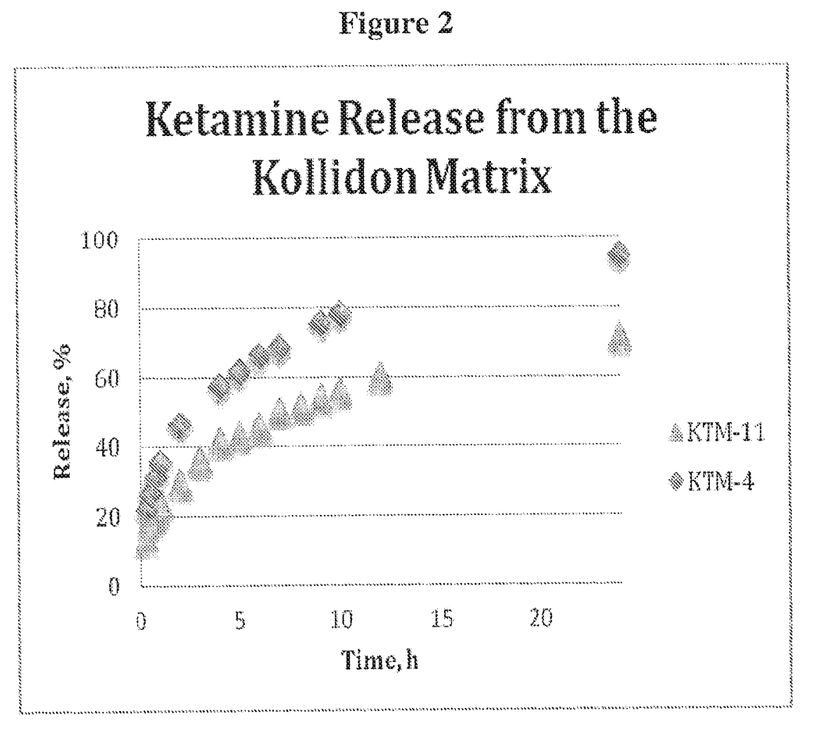
FIG. 2 is a graphical depiction of the release profile of ketamine from the Kollidon matrix, with and without lactose (compositions KTM-4 and KTM-11).
Figure 3:
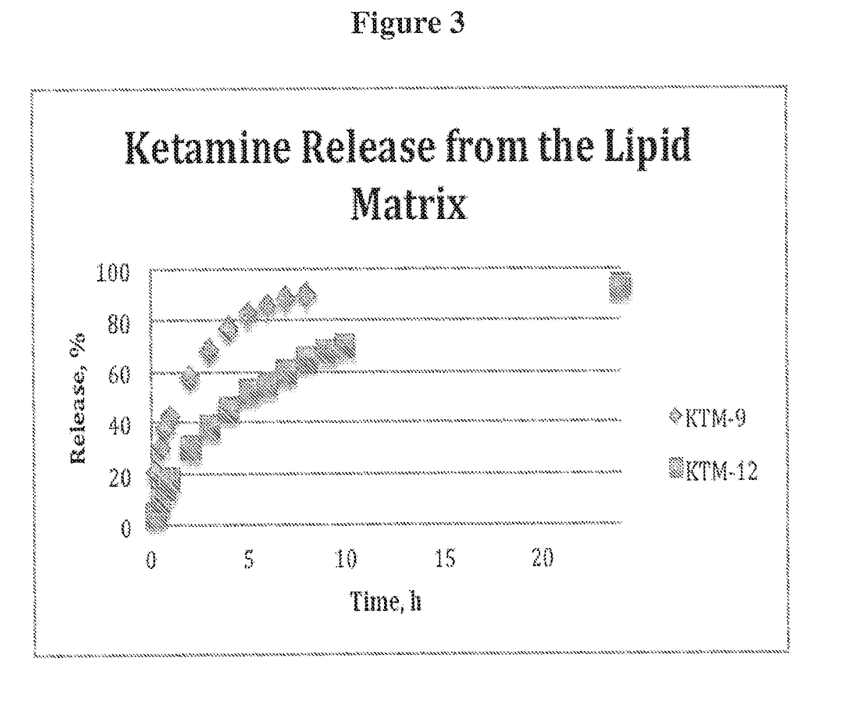
FIG. 3 is a graphical depiction of the release profile of ketamine from a lipid matrix, with and without polyacrylic acid (compositions KTM-9 and KTM-12).
Figure 4:
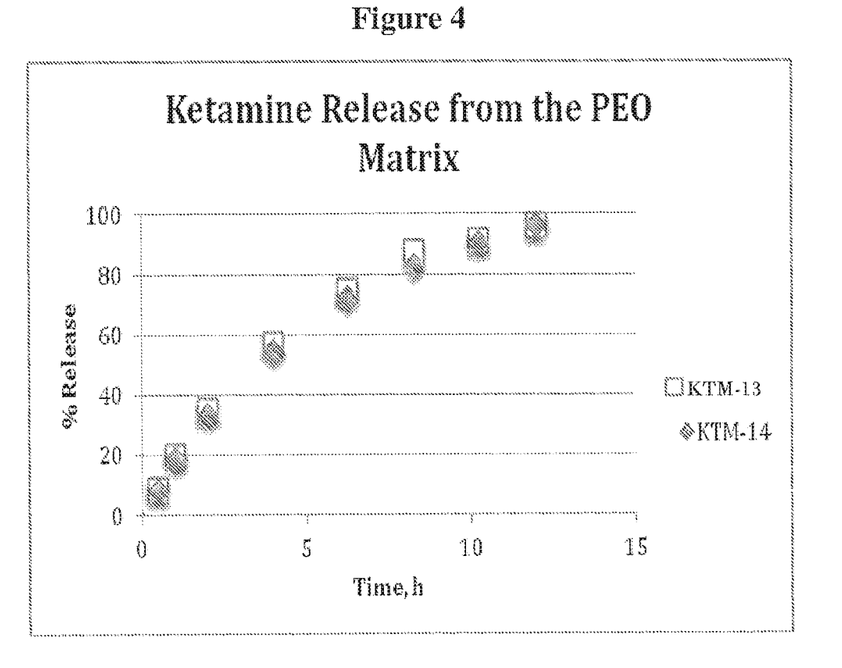
FIG. 4 is a graphical depiction of the release profile of ketamine from a PEO matrix of two different molecular weights.

A 200 mg tablets containing 20 mg of ketamine was produced using protocol similar to Example 2, with a mixture of Kollidon SR and microcrystalline cellulose to produce formulation KTM-11. The tablet composition is presented in the Table 2. The tablets displayed a good hardness, in the range of 15-20 kP, and released 56% of the drug at 10 hours and 78% at 24 hours, with full release expected to be between 36 and 48 hour time points (FIG. 2).

Addition of about 10% of lactose (formulation KTM-4) led to faster release, 72% of the drug in 10 hours, and 95% in 24 hours.

TABLE 2

Ketamine Tablet Compositions Based on the Kollidon Matrix.

| Ingredient | Manufacturer's Brand | KTM-11 | KTM-4 |
|---|---|---|---|
| Kollidon | Kollidon SR | 66.8% | 60.0% |
| Microcrystalline Cellulose | Avicel PH-200 | 22.3% | 19.0% |
| Ketamine | Ketamine Hydrochloride | 9.9% | 10.0% |
| Lactose | Lactopress 250 | 0% | 10.0% |
| Mg Stearate | Spectrum | 0.5% | 1.0% |
| Total | | 100% | 100% |

Example 4

Lipophilic Matrix Tablet Formulation of the Neuro-Attenuating Ketamine Using Glyceryl Behenate Glyceryl behenate (Compritol®, 888 ATO, Gattefosse) is a hydrophobic fatty acid ester of glycerol which may be used as a lipophilic matrix-forming agent in the manufacture of sustained-release tablets. When compressed, it forms an insoluble network structure, allowing dissolution fluid to gradually penetrate and subsequent diffusion-controlled drug release to occur through matrix channels and pores. Unlike hydrophilic matrix systems, which utilize swellable polymers such as HPMC and rely on diffusion and erosion mechanisms, drug release from insoluble matrix systems is dependent on the rate and extent of water permeation and the aqueous solubility of the drug embedded in the matrix.

The 200 mg tablets containing 20 mg of ketamine were produced using a mixture of Compritol (20%), dibasic calcium phosphate and lactose (formulation KTM-9). The tablets display a relatively low hardness, in the range of 6-7 kP, and release 92% of the drug in 8 hour. Addition of about 10% of polyacrylic acid (formulation KTM-12) leads to slowed release, 65% at 10 hour and 92% at 24 hour time points.

Example 5

Formulation of the Controlled Release Ketamine Tablet Using a Matrix Based on PEO Polyethylene oxide (PEO) is a known ingredient for the extended release solid dose forms. It has been shown to display similar formulation functional properties to HPMC. PEO-based formulations may be produced by dry granulation as well by melt extrusion, producing solid dispersions of the active pharmaceutical ingredients. As a thermoplastic polymer, PEO has glass transition temperatures in the range of 80-100° C. (depending on the molecular weight; the grade used for extended release formulation are typically within 900-7,000 KDa M average molecular weight) and could be melted during the extrusion process, solubilizing the drugs.

The 220 mg tablets containing 20 mg of ketamine were produced by dry granulation using a mixture of two different grades of PEO (MW 2,000 and 7,000 KDa), in combination with HPMC (formulations KTM-13, 14, respectively). The release properties were explored upon changing the following additional variables in the composition and processing: i) Molecular weight of PEO; (ii) Addition of polyacrylic acid as a prototypical acidic ingredient, described herein as a potential to slow down the release (formulation KTM-15); (iii) Addition of the high molecular weight PEG 8K (formulation KTM-16); (iv) annealing of the tablets for 20 min in the oven at 120° C. to mimic the mechanical properties achieved by extrusion (formulation KTM-15a).

The full compositions of tablets KTM-1346 is presented in Table 3.

The tablets displayed a relatively high hardness, in the range of 15-20 kP that increases upon annealing to 30-35 kP, indicative of acquiring tamper-resistance properties enabled by improved crush resistance. We observed little differentiation in the release properties upon changing any of the above variables, with 90-100% release achieved in about 12 h of time.

TABLE 3

Ketamine Tablet Compositions Based on the PEO Matrix

| Ingredient | Manufct. Brand | KTM-13 | KTM-14 | KTM-15 | KTM-16 |
|---|---|---|---|---|---|
| PEO, MW = 2M | Colorcon, N60K | 67.9% | 0.0% | 60.3% | 52.7% |
| PEO, MW = 7M | Colorcon, WSR-303 LEO | 0.0% | 67.9% | 0.0% | 0.0% |
| HPMC | Methocel KM100 CR | 22.6% | 22.6% | 22.6% | 22.6% |
| PEG, 8K | Spectrum | 0.0% | 0.0% | 0.0% | 15.2% |
| Ketamine | Ketamine Hydrochloride | 9.1% | 8.3% | 9.1% | 9.1% |
| Polyacrylic Acid | Carbopol 974 NF | 0.0% | 0.0% | 7.6% | 0.0% |
| Mg Stearate | Spectrum | 0.4% | 0.4% | 0.4% | 0.4% |
| Total | | 100.0% | 100.0% | 100.0% | 100.0% |

Example 6

In Vivo Performance of the Neuro-Attenuating Ketamine Tablet Formulations of the Present Invention Pharmacokinetics of the KTM-2 formulation described herein was tested in beagle dogs. In particular, one tablet of the formulation KTM-2 was administered orally with 10 ml of water to one male and one female dog that had been fasted for 12 h before administration.

The blood samples were drawn at time points 0, 0.5, 1, 2, 4, 8, and 24 h. Ketamine and norketamine were quantified in plasma using LC/MS/MS method (Agilent 1200/AB SCIEX 4000 QTRAP instrumental setup) following the general procedure as described by Nettoa et al. (Biomed. Chromatogr., 2010; using the related analytical standards of ketamine and norketamine purchased from Sigma-Aldrich.

Figure 5:
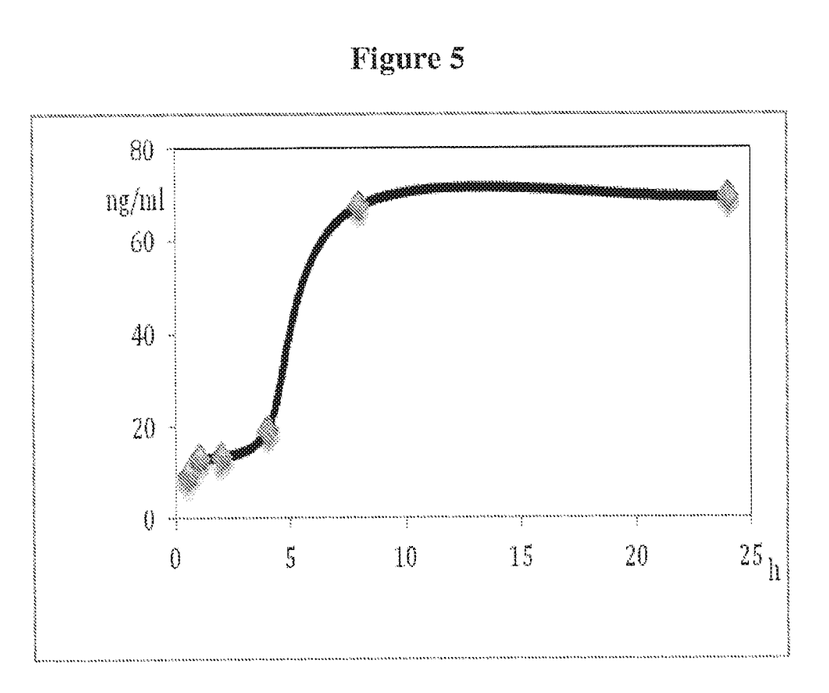
FIG. 5 is a graphical depiction of the ketamine concentration vs. time in the blood of beagle dogs after administration of tablet KTM-2.

The dogs tolerated the drug well with no observed physiological or behavioral side effects. The study showed a steady release of the drug from the matrix that is maintained for a 24 h period, with a total ketamine/norketamine concentration being within therapeutically relevant levels and no detected concentration spikes. A graph of the combined ketamine/norketamine plasma concentrations (in two dogs) vs. time is shown in FIG. 5.

This experiment confirms good in vitro-vivo correlations and validates the general pathways outlined herein related to the development and preparation of formulations of the present invention, e.g., suitable for human clinical trials.

REFERENCES

1. Correll E. G., Jahangir Maleki, J., Gracely E. J., Muir J. J., Harbut R. E. Sub-anesthetic Ketamine Infusion Therapy: A Retrospective Analysis of a Novel Therapeutic Approach to Complex Regional Pain Syndrome, *Pain Medicine*, 5(2004)263-275.

2. Zarate Jr. C. A., Brutsche N. E., Ibrahim L., Franco-Chaves J., Diazgranados N., Cravchik A., Selter J., Marquardt C. A., Liberty V., Luckenbaugh D. A. Replication of Ketamine's Antidepressant Efficacy in Bipolar Depression: A Randomized Controlled Add-On Trial, *Biol. Psych.* 71(2012)939-946.

3. Hertle D. N, Dreier J. P, Woitzik J., Hastings J. A., Bullock R., Okonkwo D. O., Shutter L. A., Vidgeon S., Strong A. J., Kowoll C., Dohmen C., Diedler J., Veltkamp R., Bruckner T., Unterberg A. W., Sakowitz O. W. Effect of Analgesics and Sedatives on the Occurrence of Spreading Depolarizations Accompanying Acute Brain Injury, *Brain,* 135(2012)2390-8.

4. Synowiec A. S., Singh D. S., Yenugadhati V., Valeriano J. P., Schramke C. J., Kelly K. M. Ketamine Use in the Treatment of Refractory Status Epilepticus, *Epilepsy Res.* 105(2013)183-8.

5. Blonk M. I., Koder B. G., van den Bemt P. M. L. A., Huygen F. J. P. M. Use of Oral Ketamine in Chronic Pain Management: A Review, *Eur. J. Pain,* 14(2010)466-472.

6. Chong C., Schug S. A., Page-Sharp M., Jenkins B., Ilett K. F. Development of a Sublingual/Oral Formulation of Ketamine for Use in Neuropathic Pain. Preliminary Findings from a Three-Way Randomized, Crossover Study, *Clin. Drug Invest.* 2009, 29(5)317.

7. Yanagihara Y., Ohtani M., Matsumoto M., Kariya S., Uchino K., Hiraishi T., Ashizawa N., Aoyama T., Yamamura Y., Iga T. Preparation of Ketamine Tablets for Treatment of Patients with Neuropathic Pain, *Yakugaku Zasshi,* 1999, 119(12)980-7.

8. Yanagihara Y, Ohtani M, Kariya S, et al. Plasma Concentration Profiles of Ketamine and Norketamine After Administration of Various Ketamine Preparations to Healthy Japanese Volunteers. *Biopharm. Drug Dispos.* 2003, 24: 37-43.

9. Analgesic Immediate and Controlled Release Pharmaceutical Compositions, U.S. Pat. No. 6,194,000 B1.

10. J. D. Nettoa, G. C. Muske, G. L. Makerb, and Robert D. Trengove, "Liquid chromatography tandem mass spectrometry for the simultaneous quantitative analysis of ketamine and medetomidine in ovine plasma", *Biomed. Chromatog.,* 2011, 25, 1374-1380.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments (e.g., such as particular pain indications); as such, each member of the list should be considered a separate embodiment.

What is claimed is:

1. A single-layer orally administered tablet composition comprising neuro-attenuating ketamine (NAKET), the NAKET comprising a polymer and ketamine, or a pharmaceutically acceptable salt of ketamine.

2. The tablet composition of claim 1, wherein the composition is adapted for maximum sustained release.

3. The tablet composition of claim 1, wherein the NAKET further comprises a water-insoluble neutrally charged non-ionic matrix; and the polymer is a polymer carrying one or more negatively charged groups.

4. The tablet composition of claim 3, wherein the non-ionic matrix is selected from cellulose-based polymers, alone or enhanced by mixing with components selected from the group consisting of starches; waxes; neutral gums; polymethacrylates; PVA; PVA/PVP blends; and mixtures thereof.

5. The tablet composition of claim 4, wherein the cellulose-based polymer is hydroxypropyl methylcellulose (HPMC).

6. The tablet composition of claim 3, wherein the polymer carrying one or more negatively charged groups is selected from the group consisting of polyacrylic acid, polylactic acid, polyglycolic acid, polymethacrylate carboxylates, cation-exchange resins, clays, zeolites, hyaluronic acid, anionic gums, salts thereof, and mixtures thereof.

7. The tablet composition of claim 6, wherein the anionic gum is selected from the group consisting of naturally occurring materials and semi-synthetic materials.

8. The tablet composition of claim 7, wherein the naturally occurring material is selected from the group consisting of alginic acid, pectin, xanthan gum, carrageenan, locust bean gum, gum arabic, gum karaya, guar gum, and gum tragacanth.

9. The table composition of claim 7, wherein the semi-synthetic material is selected from the group consisting of carboxymethyl-chitin and cellulose gum.

10. The tablet composition of claim 1, comprising an amount of ketamine therapeutically effective for the treatment of pain.

11. The tablet composition of claim 1, comprising an amount of ketamine therapeutically effective for use in the treatment of brain injury.

12. The tablet composition of claim 1, comprising an amount of ketamine therapeutically effective for the treatment of depression.

13. The tablet composition of claim 1, wherein the neuro-attenuating ketamine achieves a combined concentration of ketamine and its metabolite norketamine in plasma in the range of 10-500 ng/ml, and maintains this concentration for duration of the release period.

14. The tablet composition of claim 13, wherein the neuro-attenuating ketamine achieves a combined concentration of ketamine and its metabolite norketamine in plasma in the range of 10-20 ng/ml, and maintains this concentration for duration of the release period.

15. The tablet composition of claim 13, wherein the release period of the NAKET is greater than 4 hours.

16. The tablet composition of claim 1, wherein the pharmaceutically acceptable salt is a hydrochloride salt, aspartate salt, or succinate salt.

17. A kit for the treatment of a subject with ketamine comprising a single-layer orally administered tablet composition of claim 1 comprising neuro-attenuating ketamine (NAKET), and instructions for use in the treatment of pain, brain injury, or depression.

* * * * *